(12) United States Patent
Seibert et al.

(10) Patent No.: US 8,476,222 B2
(45) Date of Patent: Jul. 2, 2013

(54) **ISOLATED PEPTIDES FROM *ACTINOMADURA NAMIBIENSIS***

(75) Inventors: Gerhard Seibert, Darmstadt (DE); László Vértesy, Eppstein-Vockenhausen (DE); Joachim Wink, Frankfurt am Main (DE); Irvin Winkler, Frankfurt am Main (DE); Mark Broenstrup, Frankfurt am Main (DE); Holger Hoffmann, Frankfurt am Main (DE); Hans Guehring, Eltville (DE); Luigi Toti, Frankfurt am Main (DE); Roderich Süssmuth, Berlin (DE); George M. Sheldrick, Gottingen (DE); Kathrin Meindl, Gottingen (DE)

(73) Assignee: Sanofi, Paris (FR)

( * ) Notice: Subject to any disclaimer, the term of this patent is extended or adjusted under 35 U.S.C. 154(b) by 771 days.

(21) Appl. No.: 12/417,307

(22) Filed: Apr. 2, 2009

(65) Prior Publication Data
US 2009/0298904 A1 Dec. 3, 2009

Related U.S. Application Data

(63) Continuation of application No. PCT/EP2007/008294, filed on Sep. 25, 2007.

(30) Foreign Application Priority Data

Oct. 6, 2006 (EP) .................................... 06020980

(51) Int. Cl.
*A61K 38/00* (2006.01)
*A61P 31/04* (2006.01)

(52) U.S. Cl.
USPC ............................................ 514/2.3; 514/2.4

(58) Field of Classification Search
None
See application file for complete search history.

(56) References Cited

U.S. PATENT DOCUMENTS
2011/0144001 A1* 6/2011 Broenstrup et al. ........... 514/2.4

OTHER PUBLICATIONS

Chatterjee et al, Biosynthesis and Mode of Action of Lantibiotics, Chem. Rev., 2005 (105) pp. 633-683.
Goldstein et al, A40926, a New Glycopeptide Antibiotic with Anti-*Neisseria* Activity, Antimicrobial Agents and Chemotherapy, 1987 (31) 12 pp. 1961-1966.
Marazzi et al, Antibiotics GE23077, Novel Inhibitors of Bacterial RNA Polymerase. II. Structure Elucidation, J. Antibiot., 2005 (58) 4 pp. 260-267.
Sussmuth, Charakterisierung and molekularbiologische Handhabung eines bakteriellen Actinomadura-Stamms zur Aufklarung der Labyrinthopeptin-Biosynthese, Internet Article, URL:http://www.alstep.tu-berlin.de/wissdocs/suessmuth_actinom.pdf> Apr. 27, 2007.

(Continued)

*Primary Examiner* — Thomas Heard

(57) ABSTRACT

The disclosure relates to a compound of the formula (I)

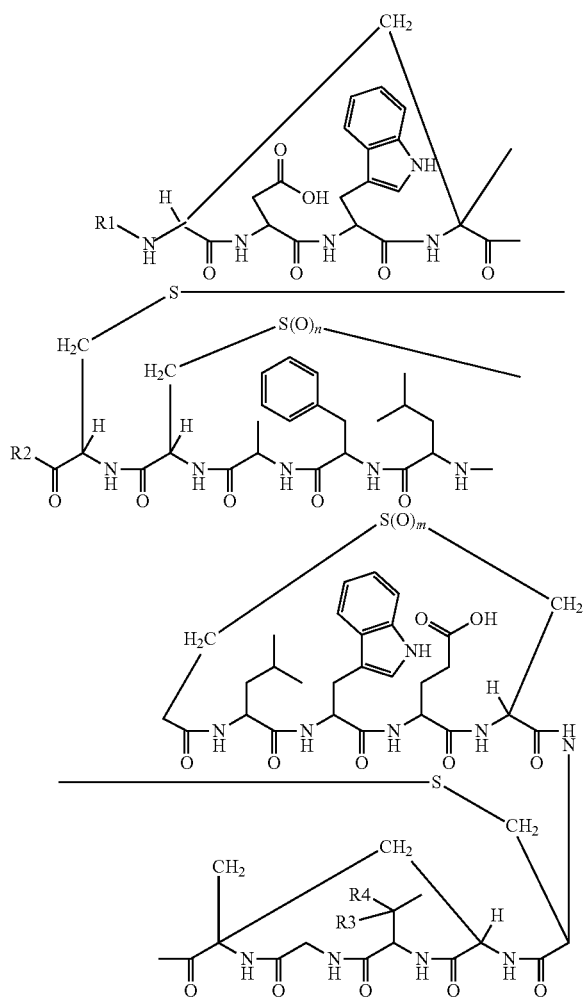

(I)

wherein
R1 is H, C(O)—($C_1$-$C_6$)alkyl or C(O)—O—($C_1$-$C_6$)alkyl;
R2 is OH, $NH_2$, NH—($C_1$-$C_6$)alkyl, NH—($C_1$-$C_4$)alkylene-phenyl or NH—($C_1$-$C_4$)alkylene-pyridyl;
R3 and R4 are independently of each other H or OH, or R3 and R4 together are =O; and
m and n are independently of one another 0, 1 or 2;
in any stereochemical form, or a mixture of any stereochemical forms in any ratio, or a physiologically acceptable salt thereof, obtainable from *Actinomadura namibiensis* (DSM 6313), and its use for the treatment of bacterial infections, viral infections and/or pain, and pharmaceutical composition comprising it.

28 Claims, No Drawings

OTHER PUBLICATIONS

Terlau et al, Conus Venoms: A Rich Source of Novel Ion Channel-Targeted Peptides, Physiol Rev., 2004 (31) pp. 41-68.

Wink et al, *Actinomadura namibiensis* sp. nov., Int. J. Systematic and Evolutionary Microbiology, 2003 (53) pp. 721-724.

Remington's Pharmaceutical Sciences, Salt Formation, 17th ed p. 1418, (1985).

Brock, et al., Mutants and Their Isolation, Biology of Microoraganisrns, 4th Edition, (1984), pp. 304-315.

Brock, et al, The Microbe in its Enyironment, Biology of Microorganisms. (1984), pp. 235-247.

Dabard, J., et al., Ruminoccin A, a New Lantibiotic Produced by a *Ruminococcus gnavus* Strain Isolated from Human Feces, Applied and Environmental Microbiolgy, (2001), pp. 4111-4118, vol. 67, No. 9.

Meindl, K., et al., Labyrinthopeptins: A New Class of Carbacyclic Lantibiotics, Angew. Chem. Int. Ed., (2010), vol. 49, pp. 1151-1154.

Mueller, et al., A Protein-Free Medium for Primary Isolation of the *Gonococcus and Meningococcus*, Proc. Soc. Expt. Biol. Med., (1941), vol. 48, pp. 330-333.

Muller, W. M., et al., In Vitro Biosynthesis of the Prepeptide of Type-III Lantibiotic Labyrinthopeptin A2 Including Formation of C-C Bond as a Post-Translational Modification, Angew. Chem. Int. Ed., (2010), vol. 49, pp. 2436-2440.

Stolp H., Microbial ecology: organisms, habitats, activites, Cambridge University Press, Cambridge, GB, 1988, p. 180.

Bauer, et al., Antibiotic Susceptibility Testing by a Standardized Single Dish Method, The American Journal of Clinical Pathology, vol. 45, No. 4, pp. 493-496, (1966).

Garber, Peptide Leads New Class of Chronic Pain Drugs, Nature Biotechnology, vol. 23, No. 4, (2005), p. 399.

Lewis, et al., Therapeutic Potential of Venom Peptides, Nature Reviews Drug Discovery, (2003), vol. 2, No. 10, p. 790-802.

Pag, et al., Multiple Activities in Lantibiotics—Models For the Design of Novel Antibiotics?, Current Pharmaceutical Design, (2002), vol. 8, No. 9, pp. 815-833.

Nomenclature and Symbolism for Amino Acids and Peptides 3AA-2 to 3AA-5 http://www.chem.qmul.ac.uk/lupac/AminoAcid/AA3t4.html—Downloaded Jun. 2012.

International Search Report for WO2008/040469 dated Apr. 10, 2008.

Data Sheet for Mueller-Hinton-Agar, downloaded from http://www.biotest.de/ww/de/pub/home.cfm, Jun. 2012.

Hochieistungs-Zellen für die Gentherapie—Neues Verfahren, Process. Aug. 1, 2006, p. 15.

Hsu, et al., NMR Study of Mersacidin and Lipid II Interaction in Dodecylphosphocholine Micelles, The Journal of Biological Chemisty, vol. 278, No. 15, pp. 13110-13117, (2003).

Kodani, et al., The SapB Morphogen is a Lantibiotic-Like Peptide Derived from the Product of the Developmental Gene ramS in *Streptomyces coelicolor*, Proc. Natl. Acad. Sci., (2004), vol. 101, No. 31, pp. 11448-11453.

* cited by examiner

ISOLATED PEPTIDES FROM ACTINOMADURA NAMIBIENSIS

CROSS REFERENCE TO RELATED APPLICATIONS

This application is a continuation of International application No. PCT/EP2007/008294 filed Sep. 25, 2007, which is incorporated herein by reference in its entirety; which claims the benefit of priority of European Patent Application No. 06020980.6, filed Oct. 6, 2006.

FIELD OF INVENTION

The present invention relates to the novel peptides isolated from *Actinomadura namibiensis* (DSM 6313), a method for its preparation and its use in the manufacture of a medicament for the treatment of bacterial infections, for the treatment of viral infections and/or for the treatment of pain.

BACKGROUND OF THE INVENTION

Several highly bridged peptides are known in the literature, for example conopeptides isolated from cone snails (for a review see e.g. Terlau & Olivera, Physiol. Rev. 2004, 84, 41-68) or the so-called lantibiotics (Chatterjee et al., Chem. Rev. 2005, 105, 633-683) from Gram-positive bacteria source. The said peptides have various utilities. The lantibiotic nisin has been used, among other utilities, as a food preservative since many years.

The conopeptides are useful, for example, for the treatment of pain, diabetes, multiple sclerosis and cardiovascular diseases and currently undergo preclinical or clinical development. Examples of conopeptides are α-GI (sequence: ECCN-PACGRHYSC*, *amidated, connectivity: 1-3,2-4) and α-GID (sequence: IRγCCSNPACRVNNOHVC, connectivity: 1-3,2-4), wherein O/Hyp is hydroxyproline and the connectivity indicates the position of the cysteine involved in each specific disulphide bonds, for example, first to third and second to fourth as in α-GID:

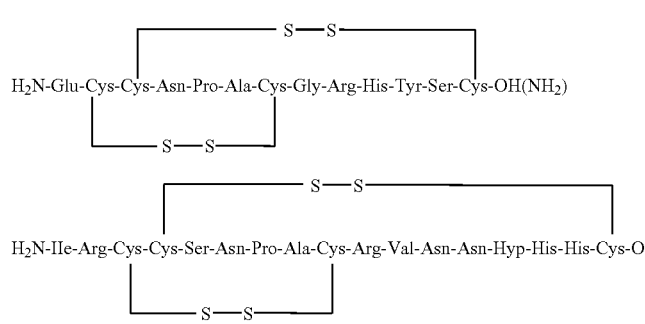

(a-GI)

(a-GID)

SUMMARY OF THE INVENTION

It has now surprisingly been found that highly bridged peptides can be isolated from microorganism strain *Actinomadura namibiensis* (DSM 6313) and are useful for the treatment of bacterial infections, viral infections and/or pain.

DETAILED DESCRIPTION OF THE INVENTION

An embodiment of the present invention is a compound of the formula (I)

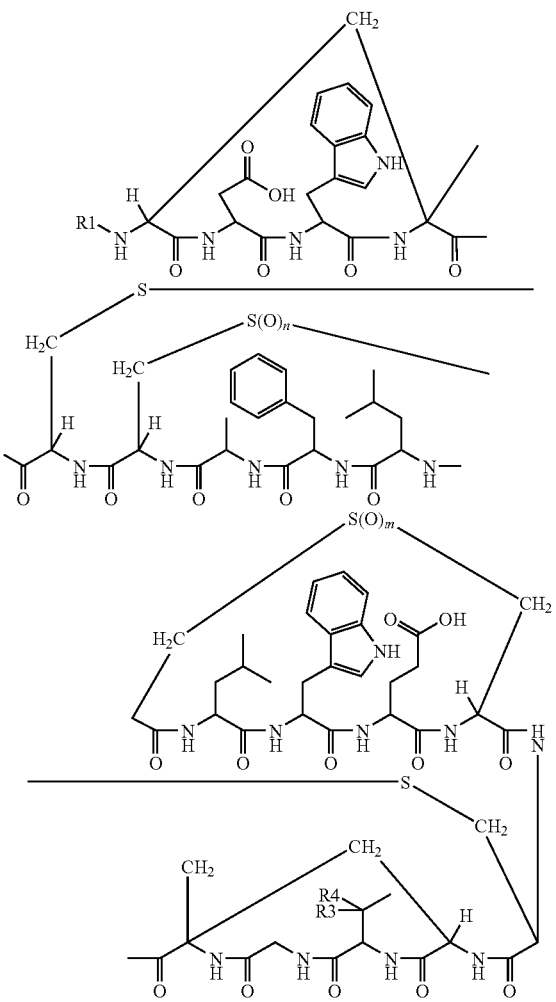

(I)

wherein
R1 is H, C(O)—($C_1$-$C_6$)alkyl or C(O)—O—($C_1$-$C_6$)alkyl;
R2 is OH, $NH_2$, NH—($C_1$-$C_6$)alkyl, NH—($C_1$-$C_4$)alkylene-phenyl or NH—($C_1$-$C_4$)alkylene-pyridyl;
R3 and R4 are independently of each other H or OH, or R3 and R4 together are =O; and
m and n are independently of one another 0, 1 or 2;

in any stereochemical form, or a mixture of any stereochemical forms in any ratio, or a physiologically tolerable salt thereof.

In a further embodiment, the compound of the formula (I) is characterized by a compound of the formula (II)

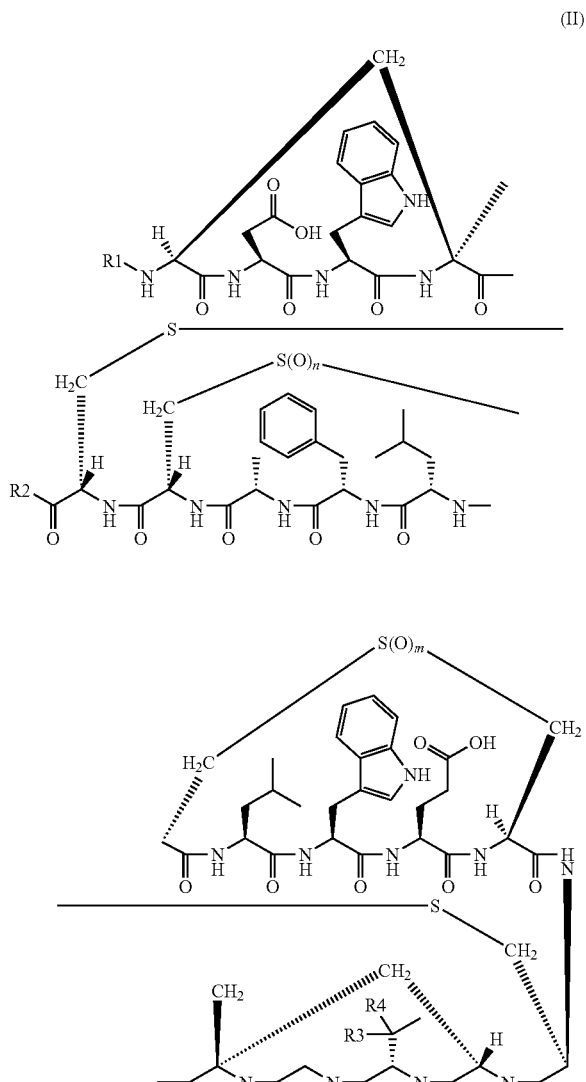

(II)

wherein R1, R2, R3, R4, m and n are as defined above.

R1 is preferably H. R2 is preferably OH. R3 and R4 are preferably H or OH wherein if R3 is OH then R4 is H, and if R3 is H then R4 is OH, or R3 and R4 together are =O. More preferred, R3 and R4 are H or OH wherein if R3 is OH then R4 is H, and if R3 is H then R4 is OH.

Preferably, m and n are both 0, or m and n are both 2, or m is 0 and n is 2, or m is 2 and n is 0. Most preferred, m and n are both 0

A further embodiment of the present invention is a compound of the formula (I) or of the formula (II) wherein
R1 is H;
R2 is OH;
R3 and R4 are H or OH wherein if R3 is OH then R4 is H, and if R3 is H then R4 is OH; and m and n are independently of one another 0, 1 or 2, preferably m and n are both 0, or m and n are both 2, or m is 0 and n is 2, or m is 2 and n is 0, particularly preferred m and n are both 0;

or a physiologically tolerable salt thereof.

Most preferred, compound (I) is characterized by a compound of the formula (III)

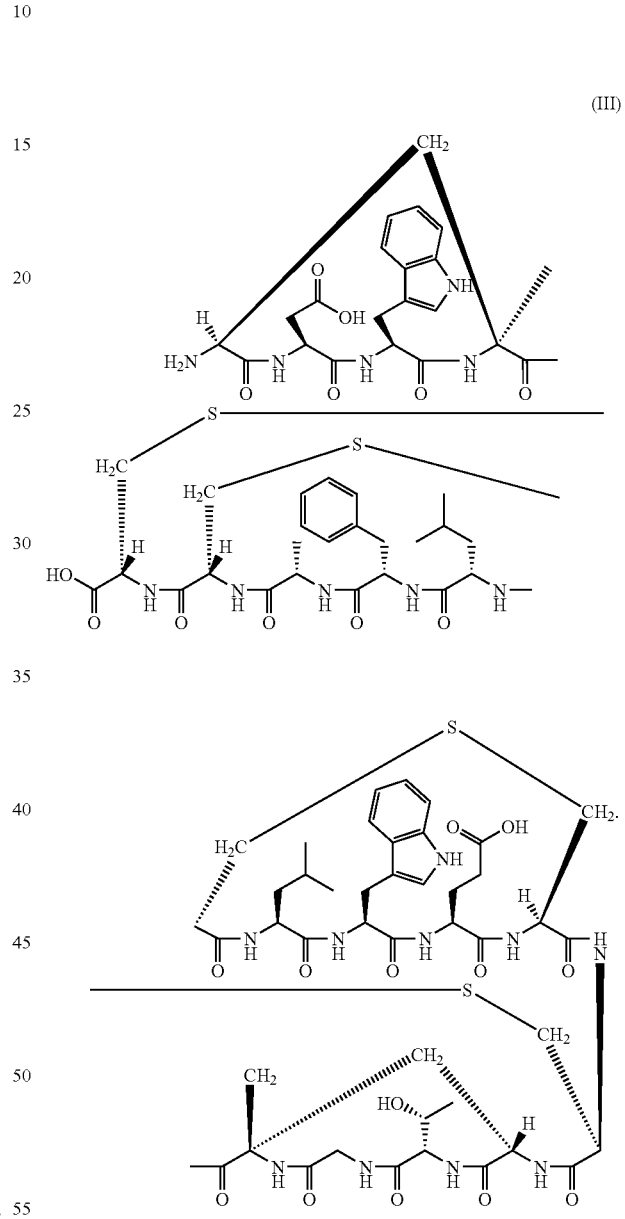

(III)

For a further characterization of the compounds of the present invention, the peptide residues were converted back to their probable precursors from ribosomal peptide synthesis. The alpha,alpha-disubstituted amino acids in residues 1 and 10 are without precedence in the literature. Said amino acid may be described as an Ala residue bridged by a methylene group and substituted at the beta-position, as shown below:

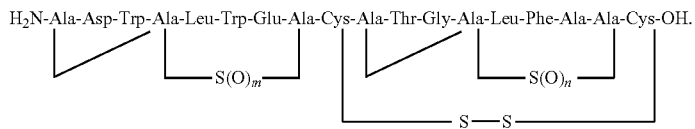

The present invention furthermore relates to all obvious chemical equivalents of the compounds of the formulae (I), (II) and (III) according to the invention. These equivalents are compounds which exhibit only a slight chemical difference, and have the same pharmacological effect, or which are converted into the compounds according to the invention under mild conditions. Said equivalents also include, for example, salts, reduction products, oxidation products, partial hydrolytic processes esters, ethers, acetals or amides of the compounds of the formulae (I), (II) and (III) as well as equivalents which the skilled person can prepare using standard methods and, in addition to this, all the optical antipodes and diastereomers and all the stereoisomeric forms.

Unless otherwise indicated, the chiral centers in the compounds of the formula (I) can be present in the R configuration or in the S configuration. The invention relates both to the optically pure compounds and to stereoisomeric mixtures, such as enantiomeric mixtures and diastereomeric mixtures.

Physiologically tolerated salts of compounds of the formulae (I), (II) and (III) are understood as being both their organic salts and their inorganic salts, as are described in Remington's Pharmaceutical Sciences (17th edition, page 1418 (1985)). Because of their physical and chemical stability and their solubility, sodium, potassium, calcium and ammonium salts are preferred, inter alia, for acid groups; salts of hydrochloric acid, sulfuric acid or phosphoric acid, or of carboxylic acids or sulfonic acids, such as acetic acid, citric acid, benzoic acid, maleic acid, fumaric acid, tartaric acid and p-toluenesulfonic acid, are preferred, inter alia, for basic groups.

The compounds of the present have been named Labyrinthopeptins throughout the text.

The invention also relates to a process for preparing a compound of the formula (I) wherein m and n are independently of one another 0, 1 or 2, which comprises
a) the strain *Actinomadura namibiensis* (DSM 6313), or one of its variants and/or mutants, being fermented under suitable conditions in a culture medium until one or more of the compounds of the formula (I) accrue(s) in the culture medium,
b) a compound of the formula (I) being isolated from the culture medium, and
c) the compound of the formula (I) being derivatized, where appropriate, and/or, where appropriate, being converted into a physiologically tolerated salt.

The invention preferably relates to a process for preparing a compound of the formula (I) wherein the compound (I) is characterized by a compound of the formula (II), more preferably the invention relates to a process for preparing a compound of the formula (I) or preferred (II) wherein m and n are both 0, or m and n are both 2, or m is 0 and n is 2, or m is 2 and n is 0.

Particularly preferred, the invention preferably relates to a process for preparing a compound of the formula (I) wherein the compound (I) is characterized by a compound of the formula (III).

The culture medium is a nutrient solution or a solid medium containing at least one customary carbon source and at least one nitrogen source as well as one or more customary inorganic salts.

The process according to the invention can be used for fermenting on a laboratory scale (milliliter to liter scale) and for fermenting on an industrial scale (cubic meter scale).

Suitable carbon sources for the fermentation are assimilable carbohydrates and sugar alcohols, such as glucose, lactose, sucrose or D-mannitol, as well as carbohydrate-containing natural products, such as malt extract or yeast extract. Examples of nitrogen-containing nutrients are amino acids; peptides and proteins and also their breakdown products, for example casein, peptones or tryptones; meat extracts; yeast extracts; gluten; ground seeds, for example from corn, wheat, beans, soya or the cotton plant; distillation residues from producing alcohol; meat meals; yeast extracts; ammonium salts; nitrates. Preference is given to the nitrogen source being one or more peptide(s) which has/have been obtained synthetically or biosynthetically. Examples of inorganic salts are chlorides, carbonates, sulfates or phosphates of the alkali metals, the alkaline earth metals, iron, zinc, cobalt and manganese. Examples of trace elements are cobalt and manganese.

Conditions which are especially suitable for forming the Labyrinthopeptins according to the invention are as follows: from 0.05 to 5%, preferably from 0.1 to 2.5%, yeast extract; from 0.2 to 5.0%, preferably from 0.1 to 2%, casitone; from 0.02 to 1.0%, preferably from 0.05 to 0.5%, $CaCl_2 \times 2H_2O$; from 0.02 to 1.5%, preferably from 0.05 to 0.7%, $MgSO_4 \times 7H_2O$ and from 0.00001% to 0.001% cyanocobalamin. The percentage values which are given are in each case based on the weight of the total nutrient solution.

The microorganism is cultured aerobically, that is, for example, submerged while being shaken or stirred in shaking flasks or fermenters, or on solid medium, where appropriate while air or oxygen is being passed in. The microorganism can be cultured in a temperature range of from about 18 to 35° C., preferably at from about 20 to 32° C., in particular at from 27 to 30° C. The pH range should be between 4 and 10, preferably between 6.5 and 7.5. The microorganism is generally cultured under these conditions for a period of from 2 to 10 days, preferably of from 72 to 168 hours. The microorganism is advantageously cultured in several steps, i.e. one or more preliminary cultures are initially prepared in a liquid nutrient medium, with these preliminary cultures then being inoculated into the actual production medium, i.e. the main culture, for example in a ratio by volume of from 1:10 to 1:100. The preliminary culture is obtained, for example, by inoculating the strain, in the form of vegetative cells or spores, into a nutrient solution and allowing it to grow for from about 20 to 120 hours, preferably for from 48 to 96 hours. Vegetative cells and/or spores can be obtained, for example, by allowing the strain to grow for from about 1 to 15 days, preferably for from 4 to 10 days, on a solid or liquid nutrient substrate, for example yeast agar.

The Labyrinthopeptin derivatives can be isolated and purified from the culture medium using known methods and taking account of the chemical, physical and biological properties of the natural substances. HPLC was used to test the concentrations of the respective Labyrinthopeptin derivatives in the culture medium or in the individual isolation steps, with the quantity of the substance formed expediently being compared with a calibration solution.

For the isolation, the culture broth or the culture together with the solid medium is optionally lyophilized, and the Labyrinthopeptin derivatives are extracted from the lyophilizate using an organic solvent or a mixture of water and an organic solvent, preferably containing 50-90% organic solvent. Examples of organic solvents are methanol and 2-propanol. The organic solvent phase contains the natural substances according to the invention; it is concentrated, where appropriate, in vacuo and subjected to further purification.

The further purification of one or more compounds according to the invention is effected by chromatography on suitable materials, preferably, for example, on molecular sieves, on silica gel, on aluminum oxide, on ion exchangers or on adsorber resins or on reversed phases (RPs). This chromatography is used to separate the Labyrinthopeptin derivatives. The Labyrinthopeptin derivatives are chromatographed using buffered, basic or acidified aqueous solutions or mixtures of aqueous and organic solutions.

Mixtures of aqueous or organic solutions are understood as being all water-miscible organic solvents, preferably methanol, 2-propanol or acetonitrile, at a concentration of from 5 to 99% organic solvent, preferably from 5 to 50% organic solvent, or else all buffered aqueous solutions which are miscible with organic solvents. The buffers which are to be used are the same as specified above.

The Labyrinthopeptin derivatives are separated, on the basis of their differing polarities, by means of reversed phase chromatography, for example on MCI (adsorber resin, Mitsubishi, Japan) or Amberlite XAD (TOSOHAAS), or on other hydrophobic materials, for example on RP-8 or RP-18 phases. In addition, the separation can be effected by means of normal-phase chromatography, for example on silica gel, aluminum oxide and the like.

Buffered, basic or acidified aqueous solutions are understood as being, for example, water, phosphate buffer, ammonium acetate and citrate buffer at a concentration of up to 0.5 M, as well as formic acid, acetic acid, trifluoroacetic acid, ammonia and triethylamine, or all commercially available acids and bases known to the skilled person, preferably at a concentration of up to 1%. In the case of buffered aqueous solutions, particular preference is given to 0.1% ammonium acetate.

The chromatography can be carried out using a gradient which began with 100% water and ended with 100% organic solvent; the chromatography was preferably run with a linear gradient of from 5 to 95% acetonitrile.

Alternatively, it is also possible to carry out a gel chromatography or chromatography on hydrophobic phases. The gel chromatography can e.g. be carried out on polyacrylamide gels or copolymer gels. The sequence of the above-mentioned chromatographic steps can be reversed.

Insofar as Labyrinthopeptins are present as stereoisomers, they can be separated using known methods, for example by means of separation using a chiral column.

The derivatization of the OH group to an ester or ether derivative is effected using methods which are known per se (J. March, Advanced Organic Chemistry, John Wiley & Sons, 4th edition, 1992), for example by means of reaction with an acid anhydride or by reaction with an di-alkyl carbonate or di-alkyl sulfate. Derivatization of the COOH group to an ester or amid derivative is effected using methods which are known per se (J. March, Advanced Organic Chemistry, John Wiley & Sons, 4th edition, 1992), for example by means of reaction with ammonia to the respective $CONH_2$ group, or with an optionally activated alkyl compound to the respective alkyl ester. Oxidation of —$CH_2$—S—$CH_2$— groups to a —$CH_2$—S(O)—$CH_2$— or a —$CH_2$—$S(O)_2$—$CH_2$— group can be achieved upon exposing the respective Labyrinthopeptin derivative to oxygen or air.

An isolate of the microorganism strain *Actinomadura namibiensis* was deposited under identification reference FH-A 1198 in the Deutsche Sammlung von Mikroorganismen und Zellkulturen [German Collection of Microorganisms and Cell Cultures] GmbH (DSMZ), Mascheroder Weg 1B, 38124 Braunschweig, Germany, in accordance with the rules of the Budapest treaty, on 23, Jan. 1991 under the following number: DSM 6313. Microorganism strain *Actinomadura namibiensis* is further described by Wink et al. in International Journal of Systematic and Evolutionary Microbiology 2003, 53, 721-724.

Instead of the strain *Actinomadura namibiensis* (DSM 6313), it is also possible to use its mutants and/or variants which synthesize one or more of the compounds according to the invention.

A mutant is a microorganism in which one or more genes in the genome has/have been modified, with the gene, or the genes, which is/are responsible for the ability of the organism to produce the compound according to the invention remaining functional and heritable.

Such mutants can be produced, in a manner known per se, using physical means, for example irradiation, as with ultraviolet rays or X-rays, or chemical mutagens, such as ethyl methanesulfonate (EMS); 2-hydroxy-4-methoxybenzophenone (MOB) or N-methyl-N'-nitro-N-nitrosoguanidine (MNNG), or as described by Brock et al. in "Biology of Microorganisms", Prentice Hall, pages 238-247 (1984).

A variant is a phenotype of the microorganism. Microorganisms have the ability to adapt to their environment and therefore exhibit highly developed physiological flexibility. All the cells of the microorganism are involved in the phenotypic adaptation, with the nature of the change not being genetically conditioned and being reversible under altered conditions (H. Stolp, Microbial ecology: organism, habitats, activities. Cambridge University Press, Cambridge, GB, page 180, 1988).

Screening for mutants and/or variants which synthesize one or more of the compounds according to the invention is achieved by optionally lyophilizing the fermentation medium and extracting the lyophilizate or the fermentation broth with an organic solvent or a mixture of water and an organic solvent as defined above, and analyzing by means of HPLC or TLC or by testing the biological activity.

The fermentation conditions may be applied to *Actinomadura namibiensis* (DSM 6313) and for mutants and/or variants thereof.

A further embodiment of the present invention is the use of a compound of the formula (I), preferably a compound of the formula (II) or (III), as defined above, for the treatment of bacterial infections, especially bacterial infections caused by Gram-positive bacteria, for the treatment of viral infections and/or for the treatment of pain, especially neuropathic pain or inflammatory triggered pain.

The above described medicament (also referred to as pharmaceutical preparation or pharmaceutical composition) contains an effective amount of at least one compound of the formula (I), in any stereochemical form, or a mixture of any stereochemical forms in any ratio, or a physiologically tolerable salt or chemical equivalent thereof, as described above, and at least one pharmaceutically acceptable carrier, preferably one or more pharmaceutically acceptable carrier substances (or vehicles) and/or additives (or excipients).

The medicament can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The medicaments according to the invention are prepared in a manner known per se and familiar to one skilled in the art, pharmaceutically acceptable inert inorganic and/or organic carrier substances and/or additives being used in addition to the compound(s) of the formula (I) in any stereochemical form, or a mixture of any stereochemical forms in any ratio, or a physiologically tolerable salt or chemical equivalent thereof, as described above. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of a compound of the formula (I) and/or their physiologically acceptable salts and/or their prodrugs. The amount of the active ingredient of the formula (I) in any stereochemical form, or a mixture of any stereochemical forms in any ratio, or a physiologically tolerable salt or chemical equivalent thereof, as described above, in the medicaments normally is from about 0.5 to about 1000 mg, preferably from about 1 to about 500 mg.

In addition to the active ingredients of the formula (I) in any stereochemical form, or a mixture of any stereochemical forms in any ratio, or a physiologically tolerable salt or chemical equivalent thereof, as described above, and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) in any stereochemical form, or a mixture of any stereochemical forms in any ratio, or a physiologically tolerable salt or chemical equivalent thereof. In case a pharmaceutical preparation contains two or more compounds of the formula (I), the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I), the pharmaceutical preparations can also contain one or more other therapeutically or prophylactically active ingredients.

When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

EXAMPLE 1

Preparation of a Cryoculture of *Actinomadura namibiensis* (DSM 6313)

100 ml culture medium (10 g starch, 2 g yeast extract, 10 g glucose, 10 g glycerine, 2.5 g cornsteep powder, 2 g peptone, 1 g NaCl, 3 g $CaCO_3$ in 1 l tap water, pH 7.2 before sterilization) were seeded with the strain *Actinomadura namibiensis* (DSM 6313) in a sterile 500 ml Erlenmeyer flask and incubated for 72 hours at 27° C. and 120 rpm on a shaker. Subsequently, 1 ml of the culture and 1 ml sterile conservation solution (20 g glycerine, 10 g saccharose, 70 ml de-ionized water) were mixed and stored at −80° C. Alternatively, small pieces of a well-grown culture on agar were transferred Cryotubes® (Vangard International) with 1.5 ml 50% sterile glycerine solution and stored at −196° C. in liquid nitrogen.

EXAMPLE 2

Preparation of Labyrinthopeptins

A sterile 500 ml Erlenmeyer flask containing 100 ml of the culture medium described in Example 1 was seeded with a culture of *Actinomadura namibiensis* (DSM 6313) which was grown on an agar plate and was incubated at 27° C. and 120 rpm on a shaker. After 72 hours, further Erlenmeyer flasks containing the same culture medium in the same amount were seeded with 2 ml of this pre-culture each and incubated under identical conditions for 168 hours. Alternatively, a 300 ml Erlenmeyer flask containing 100 ml of the culture medium described in Example 1 was seeded with a culture of *Actinomadura namibiensis* (DSM 6313) and incubated at 25° C. and 180 rpm. After 72 hours, further Erlenmeyer flasks containing the same culture medium in the same amount were seeded with 5 ml of this pre-culture each and incubated under identical conditions for 168 hours.

EXAMPLE 3

Isolation of Labyrinthopeptins

2% Hyflo Super-cel diatomaceous earth (Hyflo Supercell; VWR Darmstadt, Germany) were given to 10 l of the culture broth containing according to Example 2 and the culture was filtrated through a filter press in order to separate the culture solution from the mycel. The filtrate was given on to column containing 1 l Amberlite XAD-16 resin (column diameter: 5.5 cm, column height: 42 cm), and washed with 5 l deionized water and 5 l 20% methanol in water. The Labyrinthopeptin was eluted with 5 l 60% methanol in water and 5 l 80% methanol in water. The Labyrinthopeptin containing fractions were identified by HPLC-DAD and LC-ESI-MS, collectively concentrated on a rotary evaporator until an aqueous residue was obtained and subsequently freeze-dried. 300 mg crude product was obtained.

EXAMPLE 4

High Performance Liquid Chromatography with Diode-array Detection (HPLC-DAD) of Labyrinthopeptins Column: Nucleosil 100–$C_{18}$; 20+125 mm×4.6 mm, 5μ (Machery-Nagel)
Mobile phase: 0.1% $H_3PO_4$ in water (Eluent A) and acetonitrile (Eluent B) linear gradient from 0% to 100% Eluent B in Eluent A over a period of 15 minutes
Flow: 2 ml per minute
Detection by UV/Vis absorption yielded peaks at 210, 230, 260, 280, 310, 360, 435 and 500 nm.
The retention time of the Labyrinthopeptin of the formula (II): 7.75 minutes.

EXAMPLE 5

High Performance Liquid Chromatography with Electrospray Ionization Mass Spectroscopy (HPLC-ESI-MS) of Labyrinthopeptins Column: Purospher RP-18e; 125 mm (4 mm, 5μ (Agilent)
Mobile phase: 0.1% trifluoro acetic acid in Wasser Water (Eluent A) and 0.1% trifluoro acetic acid in Acetonitrile (Eluent B) linear gradient from 5% to 100% Eluent B in Eluent A over a period of 10 minutes
Flow: 1.5 ml per minute. The flow to the ES interface of the mass spectrometer was reduced to 0.4 ml per minute via a T splitter.
Detection by UV absorbtion at 210 nm and ESI-MS (positive mode) wherein an ion trap was used as mass analyzer.
The retention time of the Labyrinthopeptin of the formula (III) was 5.9 minutes. The molecular mass was 1922 Da.

EXAMPLE 6

Purification of Labyrinthopeptins

The Labyrinthopeptin crude product obtained according to Example 3 (300 mg) was dissolved in a mixture of dimethylsulfoxide, methanol and water (1:3:6) and the components were separated via chromatography on a Nucleosil 100–$C_{18}$ column (particle size: 10μ, column size: 250×16 mm) using isocratic elution (water+0.1% formic acid/methanol 35:65) at a flow rate of 20 ml per minute. The fractions were analyzed with HPLC (cf. Example 4). 62 mg Labyrinthopeptin of the formula (III) was obtained in 99% purity.

EXAMPLE 7

General characteristics of Labyrinthopeptin (III)

The compound of the formula (III) was oxidized upon exposure to air to the respective sulfoxides. The compound of the formula (III) contains 2 cis-amides between [2]Asp-[3]Trp and [11]Thr-[12]Gly.

EXAMPLE 8

High resolving ESI-FTICR-mass Spectrometry

A solution of the Labyrinthopeptin of the formula (III) in Methanol (c=0.2 mg/ml) was admitted through a syringe pump at a flow rate of 2 μl/min to a Bruker Apex III FTICR MS (7T magnet) equipped with an electrospray source. Spectra were recorded in the positive mode using an external calibration.

| | |
|---|---|
| m/z observed in Da (z = 2, M + 2Na⁺ ion) | 984.3333 |
| Exact, mono-isotopic mass of neutral [M] | 1922.6872 |
| Theoretical mass [M] for $C_{85}H_{110}N_{20}O_{24}S_4$ | 1922.6885 |
| Molecular formula | $C_{85}H_{110}N_{20}O_{24}S_4$ |

EXAMPLE 9

Amino Acid Analysis

Hydrolysis: Labyrinthopeptin (III) (0.05 mg) was hydrolyzed in nitrogen atmosphere with 6 N HCl, 5% phenol at 110° C. for 24 h. The hydrolysate was dried in a stream of nitrogen.

Achiral GC-MS: The hydrolysate was heated with bis-(Trimethylsilyl)trifluoro-acetamide (BSTFA)/Acetonitrile (1:1) at 150° C. for 4 h. For GC-MS experiments a DB5-fused-silica-capillary (I=15 m×0.25 μm fused silica coated with dimethyl-(5%-phenylmethyl)-polysiloxane, $d_f$=0.10 μm; temperature program: T=65°/3'/6/280° C.) was used.

Chiral GC-MS: The hydrolysate was esterified with 200 μl 2 N HCl in ethanol at 110° C. for 30 min and dried. Subsequently, the mixture was acylated with 25 μl TFAA in 100 μl dichloromethane at 110° C. 10 min for and dried. For GC-MS a fused-silica-capillary was used (I=22 m×0.25 μm fused silica coated with chirasil-S-Val (Machery-Nagel), $d_f$=0.13 μm; temperature program: T=55°/3'/3,2/180° C.).

| | | configuration |
|---|---|---|
| Amino acids | 1 Ala, 1 Thr, 2 Leu, 1 Asp, 2 Cys, 1 Phe, 1 Glu, 2 Trp, 1 Gly | all S-amino acids |

EXAMPLE 10

NMR Spectroscopy

2-D NMR spectra (COSY, TOCSY, NOESY, HSQC, HMBC) were measured on an AMX 600 MHz NMR spectrometer (Bruker, Karlsruhe, Germany) equipped with a 5 mm Z-Grad triple resonance probe head and on a DRX500 NMR spectrometer (Bruker, Karlsruhe, Germany) equipped with a 5 mm Z-Grad broad band inverse probehead. The following table shows the signals obtained in the measurements.

NMR data for the Labyrinthopeptin of the formula (III) in DMSO-d6:

| | |
|---|---|
| $^1$H | 0.68; 0.71; 0.75; 0.78; 1.05; 1.07; 1.10; 1.35; 1.40; 1.42; 1.49; 1.90; 1.96; 2.00; 2.10; 2.17; 2.26; 2.77; 2.86; 2.90; 2.97; 3.03; 3.14; 3.16; 3.18; 3.18; 3.20; 3.24; 3.29; 3.30; 3.39; 3.59; 3.67; 3.67; 3.72; 3.99; 4.02; 4.03; 4.10; 4.13; 4.14; 4.16; 4.19; 4.34; 4.36; 4.45; 4.49; 4.59; 6.96; 7.26; 7.00; 7.04; 7.08; 7.08; 7.10; 7.18; 7.22; 7.23; 7.24; 7.24; 7.31; 7.35; 7.36; 7.42; 7.51; 7.53; 7.65; 7.65; 7.69; 7.77; 7.84; 7.98; 8.00; 8.01; 8.56; 10.80; 10.81. |
| $^{13}$C | 19.7; 21.3; 21.4; 22.6; 23.04; 23.2; 23.7; 26.4; 26.4; 27.1; 33.4; 35.2; 35.4; 36.7; 38.3; 40.0; 40.5; 40.7; 40.8; 40.8; 41.2; 41.2; 43.4; 48.4; 48.7; 49.0; 51.2; 51.4; 52.5; 52.6; 52.7; 53.2; 53.5; 54.0; 56.9; 60.0; 60.3; 66.4; 109.8; 110.6; 111.2; 111.2; 117.4; 118.1; 118.1; 118.2; 120.7; 120.7; 122.1; 123.4; 126.5; 127.2; 127.3; 127.8; 129.4; 136.0; 136.1; 136.6; 140.8; 169.4; 173.0; 174.3; 176.9. |

EXAMPLE 11

X-ray Crystallography of Labyrintopeptin (III)

Crystallization conditions: The protein was dissolved in 0.02 M Tris pH 8.2 (concentration 7 mg/ml). Crystals grew at room temperature by vapor drop diffusion from a 1:1 mixture of the protein solution with a solution of 60% ethanol, 0.75% PEG 6000, 0.025 M sodium acetate and 0.05 M sodium chloride. Crystals grew within about one week.

Measurement: X-ray data were collected on a Bruker 3-circle diffractometer with rotating anode and mirror monochromated CuK-alpha radiation. Intensities were collected on a SMART 6000 CCD area detector.

Crystal Data:

| Formula | Na N$_{20}$ C$_{85}$ S$_4$ O$_{48}$ | Na C$_{85}$ N$_{20}$ O$_{24}$ S$_4$ |
|---|---|---|
| Formula weight | 2220.29 | 1834.82 |
| Crystal system | orthorhombic | |
| Space group | P 21 21 2 (no. 18) | |
| Unit cell dimensions | a = 41.1360 Å | |
| | b = 12.8850 Å | |
| | c = 25.5900 Å | |
| Cell volume | 13563.66 Å$^3$ | |
| Z | 4 | |
| Density, calculated | 1.087 g/cm$^3$ | |
| Pearson code | oP732 | |
| Formula type | NO4P20Q48R85 | |
| Wyckoff sequence | c$^{181}$b$^3$a | |

Atomic Coordinates:

| No. | Atom | Atom No. | x | y | z | e$^-$-density |
|---|---|---|---|---|---|---|
| 0 | Na | NA | 0.26282 | 1.11533 | −0.20024 | 1.0 |
| 1 | N | 18NH | 0.16643 | 0.62593 | 0.30751 | |
| 2 | C | 18Ca | 0.15933 | 0.69120 | 0.26221 | |
| 3 | C | 18Cb | 0.12264 | 0.69329 | 0.24928 | |
| 4 | S | 18Sg | 0.11248 | 0.78619 | 0.19945 | |
| 5 | C | 18CO | 0.16446 | 0.80225 | 0.28144 | |
| 6 | O | 18OC1 | 0.15211 | 0.83361 | 0.32212 | |
| 7 | O | 18OC3 | 0.17868 | 0.86558 | 0.25381 | 0.290 |
| 8 | O | 18OC2 | 0.18240 | 0.86116 | 0.25780 | 0.710 |
| 9 | N | 17NH2 | 0.17255 | 0.50082 | 0.39461 | 0.570 |
| 10 | C | 17Ca2 | 0.19839 | 0.49670 | 0.35604 | 0.570 |
| 11 | N | 17NH1 | 0.17994 | 0.49779 | 0.40196 | 0.430 |
| 12 | C | 17Ca1 | 0.20056 | 0.49833 | 0.35678 | 0.430 |
| 13 | C | 17Cb | 0.20165 | 0.38479 | 0.33630 | 1.0 |
| 14 | S | 13S1 | 0.16523 | 0.32006 | 0.32001 | |
| 15 | C | 17CO | 0.19312 | 0.57036 | 0.31036 | |
| 16 | O | 17OC | 0.21276 | 0.57136 | 0.27366 | |
| 17 | N | 16NH1 | 0.11776 | 0.48825 | 0.45694 | 0.570 |
| 18 | C | 16Ca1 | 0.14725 | 0.54296 | 0.47554 | 0.570 |
| 19 | C | 16Cb2 | 0.14824 | 0.52387 | 0.53451 | 0.570 |
| 20 | C | 16CO2 | 0.17744 | 0.51223 | 0.44580 | 0.570 |
| 21 | O | 16OC2 | 0.20586 | 0.50283 | 0.46026 | 0.570 |
| 22 | N | 16NH2 | 0.12522 | 0.46605 | 0.47460 | 0.430 |
| 23 | C | 16Ca2 | 0.15695 | 0.50741 | 0.49039 | 0.430 |
| 24 | C | 16Cb1 | 0.17666 | 0.42678 | 0.52110 | 0.430 |
| 25 | C | 16CO1 | 0.17829 | 0.54862 | 0.44623 | 0.430 |
| 26 | O | 16OC1 | 0.19399 | 0.62818 | 0.45350 | 0.430 |
| 27 | N | 15NH | 0.08606 | 0.28654 | 0.38875 | 1.0 |
| 28 | C | 15Ca | 0.08545 | 0.33846 | 0.43783 | |
| 29 | C | 15Cb | 0.07342 | 0.26519 | 0.48191 | |
| 30 | C | 15Cg | 0.07342 | 0.31743 | 0.53443 | |
| 31 | C | 15Cd1 | 0.09641 | 0.30051 | 0.57015 | |
| 32 | C | 15Ce1 | 0.09892 | 0.34692 | 0.61802 | |
| 33 | C | 15Cz | 0.07361 | 0.41607 | 0.62963 | |
| 34 | C | 15Ce2 | 0.04891 | 0.43679 | 0.59512 | |
| 35 | C | 15Cd2 | 0.04787 | 0.38914 | 0.54580 | |
| 36 | C | 15CO2 | 0.11795 | 0.38518 | 0.45303 | 0.570 |
| 37 | O | 15OC2 | 0.14083 | 0.32503 | 0.46100 | 0.570 |
| 38 | C | 15CO1 | 0.11985 | 0.37400 | 0.45272 | 0.430 |
| 39 | O | 15OC1 | 0.14260 | 0.31215 | 0.44467 | 0.430 |
| 40 | N | 14NH | 0.09663 | 0.22957 | 0.28367 | 1.0 |
| 41 | C | 14Ca | 0.06493 | 0.21832 | 0.30973 | |
| 42 | C | 14Cb | 0.05881 | 0.10260 | 0.32228 | |
| 43 | C | 14Cg | 0.06148 | 0.01917 | 0.28163 | |
| 44 | C | 14Cd1 | 0.05246 | −0.08320 | 0.30793 | |
| 45 | C | 14Cd2 | 0.04038 | 0.05153 | 0.23556 | |
| 46 | C | 14CO | 0.06073 | 0.27513 | 0.35936 | |
| 47 | O | 14OC | 0.03420 | 0.31036 | 0.37413 | |
| 48 | N | 13NH | 0.14348 | 0.21739 | 0.21016 | |
| 49 | C | 13Ca | 0.13259 | 0.32131 | 0.22415 | |
| 50 | C | 13Cb | 0.15887 | 0.37393 | 0.25639 | |
| 51 | C | 13CO | 0.10174 | 0.31603 | 0.25729 | |
| 52 | O | 13OC | 0.08431 | 0.39162 | 0.25920 | |
| 53 | N | 12NH | 0.13789 | 0.04315 | 0.10383 | |
| 54 | C | 12Ca | 0.14494 | 0.06092 | 0.15913 | |
| 55 | C | 12CO | 0.12665 | 0.15374 | 0.17941 | |
| 56 | O | 12OC | 0.09846 | 0.17540 | 0.16440 | |
| 57 | N | 11NH | 0.18026 | 0.23392 | 0.10274 | |
| 58 | C | 11Ca | 0.18245 | 0.14769 | 0.06491 | |
| 59 | C | 11Cb | 0.21437 | 0.08040 | 0.07601 | |
| 60 | O | 11Og | 0.24067 | 0.15367 | 0.06932 | |
| 61 | C | 11Cg | 0.21483 | −0.00652 | 0.03877 | |
| 62 | C | 11CO | 0.15298 | 0.08188 | 0.06213 | |
| 63 | O | 11OC | 0.14289 | 0.05192 | 0.01723 | |
| 64 | N | 10NH | 0.15427 | 0.48630 | 0.10547 | |
| 65 | C | 10Ca | 0.15553 | 0.39216 | 0.13693 | |
| 66 | C | 10Cb | 0.12680 | 0.38774 | 0.17495 | |
| 67 | C | 10CO | 0.15563 | 0.30214 | 0.09785 | |
| 68 | O | 10OC | 0.13341 | 0.29174 | 0.06737 | |
| 69 | N | 9NH | 0.15921 | 0.62732 | 0.02599 | |
| 70 | C | 9Ca | 0.17078 | 0.65813 | 0.07761 | |
| 71 | C | 9Cb1 | 0.15364 | 0.74568 | 0.10696 | 0.650 |

| No. | Atom | Atom No. | x | y | z | e⁻-density |
|---|---|---|---|---|---|---|
| 72 | S | 9Sg2 | 0.11348 | 0.70773 | 0.12986 | 0.650 |
| 73 | C | 9Cb2 | 0.14430 | 0.73147 | 0.09699 | 0.350 |
| 74 | S | 9Sg1 | 0.15631 | 0.80140 | 0.15424 | 0.350 |
| 75 | C | 9CO | 0.17309 | 0.56593 | 0.11423 | 1.0 |
| 76 | O | 9OC | 0.19300 | 0.56593 | 0.15084 | |
| 77 | N | 8NH | 0.18541 | 0.52953 | −0.09746 | |
| 78 | C | 8Ca | 0.16349 | 0.52728 | −0.05346 | |
| 79 | C | 8Cb | 0.15665 | 0.41428 | −0.03791 | |
| 80 | S | 4S1 | 0.14207 | 0.33194 | −0.08922 | |
| 81 | C | 8CO | 0.17870 | 0.57819 | −0.00528 | |
| 82 | O | 8OC | 0.20763 | 0.56423 | 0.00430 | |
| 83 | N | 7NH | 0.20632 | 0.49826 | −0.20125 | |
| 84 | C | 7Ca | 0.21045 | 0.59830 | −0.17558 | 1.0 |
| 85 | C | 7Cb | 0.20977 | 0.68941 | −0.21403 | |
| 86 | C | 7Cg | 0.23965 | 0.69290 | −0.24846 | |
| 87 | C | 7Cd | 0.27179 | 0.70780 | −0.21942 | |
| 88 | O | 7O2 | 0.27356 | 0.77789 | −0.18617 | |
| 89 | O | 7O2 | 0.29422 | 0.64688 | −0.23185 | |
| 90 | C | 7CO | 0.18551 | 0.60947 | −0.13036 | |
| 91 | O | 7OC | 0.16934 | 0.68669 | −0.12474 | |
| 92 | N | 6NH | 0.14508 | 0.31502 | −0.23408 | |
| 93 | C | 6Ca | 0.17581 | 0.36438 | −0.24779 | |
| 94 | C | 6Cb | 0.17865 | 0.38440 | −0.30618 | |
| 95 | C | 6Cg | 0.21065 | 0.42228 | −0.32263 | |
| 96 | C | 6Cd1 | 0.24023 | 0.37835 | −0.31634 | |
| 97 | N | 6Ne | 0.26396 | 0.43927 | −0.33810 | |
| 98 | C | 6Ce2 | 0.24957 | 0.52674 | −0.35877 | |
| 99 | C | 6Cd2 | 0.21551 | 0.51704 | −0.34959 | |
| 100 | C | 6Ce1 | 0.19382 | 0.59341 | −0.36554 | |
| 101 | C | 6Cz1 | 0.20739 | 0.67707 | −0.39101 | |
| 102 | C | 6Ch | 0.24169 | 0.68111 | −0.39910 | |
| 103 | C | 6Cz2 | 0.26459 | 0.61009 | −0.38421 | |
| 104 | C | 6CO | 0.17783 | 0.46644 | −0.21817 | |
| 105 | O | 6OC | 0.15276 | 0.51859 | −0.21294 | |
| 106 | N | 5NH | 0.09092 | 0.22755 | −0.18031 | |
| 107 | C | 5Ca | 0.10636 | 0.17447 | −0.22462 | |
| 108 | C | 5Cb | 0.08579 | 0.17788 | −0.27331 | |
| 109 | C | 5Cg1 | 0.06556 | 0.08855 | −0.29223 | 0.400 |
| 110 | C | 5Cd2 | 0.05562 | 0.00295 | −0.25553 | 0.400 |
| 111 | C | 5CD3 | 0.03406 | 0.13232 | −0.31950 | 0.400 |
| 112 | C | 5Cg2 | 0.05122 | 0.12511 | −0.26843 | 0.600 |
| 113 | C | 5Cd1 | 0.05227 | 0.02119 | −0.24021 | 0.600 |
| 114 | C | 5Cd2 | 0.03647 | 0.22422 | −0.25795 | 0.600 |
| 115 | C | 5CO | 0.14049 | 0.21405 | −0.23552 | 1.0 |
| 116 | O | 5OC | 0.16220 | 0.15250 | −0.24447 | |
| 117 | N | 4NH | 0.04424 | 0.29531 | −0.10297 | |
| 118 | C | 4Ca | 0.07828 | 0.26318 | −0.08968 | |
| 119 | C | 4Cb | 0.09901 | 0.36213 | −0.08847 | |
| 120 | C | 4CO | 0.09150 | 0.19084 | −0.13193 | |
| 121 | O | 4OC | 0.10378 | 0.10656 | −0.12020 | |
| 122 | N | 3NH | −0.02049 | 0.37136 | −0.10602 | |
| 123 | C | 3Ca | −0.01386 | 0.26387 | −0.12087 | |
| 124 | C | 3Cb | −0.02263 | 0.24478 | −0.17726 | |
| 125 | C | 3Cg | −0.05642 | 0.26752 | −0.19336 | |
| 126 | C | 3Cd1 | −0.08244 | 0.28646 | −0.16303 | |
| 127 | N | 3Ne | −0.10966 | 0.30431 | −0.19328 | |
| 128 | C | 3Ce2 | −0.10052 | 0.29888 | −0.24451 | |
| 129 | C | 3Cd2 | −0.06697 | 0.27528 | −0.24627 | |
| 130 | C | 3Ce1 | −0.05275 | 0.26512 | −0.29539 | |
| 131 | C | 3Cz1 | −0.07001 | 0.27753 | −0.33970 | |
| 132 | C | 3Ch | −0.10351 | 0.30097 | −0.33634 | |
| 133 | C | 3Cz2 | −0.11905 | 0.31339 | −0.29019 | |
| 134 | C | 3CO | 0.02125 | 0.22763 | −0.11313 | |
| 135 | O | 3OC | 0.02703 | 0.13349 | −0.11547 | |
| 136 | N | 2NH | 0.00873 | 0.33093 | −0.00078 | |
| 137 | C | 2Ca | −0.02584 | 0.34024 | −0.01079 | |
| 138 | C | 2Cb | −0.04293 | 0.38712 | 0.03587 | |
| 139 | C | 2Cg | −0.07852 | 0.41234 | 0.02763 | |
| 140 | O | 2Od1 | −0.09430 | 0.35452 | −0.00285 | |
| 141 | O | 2Od2 | −0.09060 | 0.48825 | 0.05303 | |
| 142 | C | 2CO | −0.02912 | 0.40784 | −0.06006 | |
| 143 | O | 2OC | −0.03851 | 0.49903 | −0.05444 | |
| 144 | N | 1NH | 0.07381 | 0.20163 | 0.05701 | |
| 145 | C | 1Ca | 0.06250 | 0.25417 | 0.00903 | |
| 146 | C | 1Cb | 0.07969 | 0.20450 | −0.03763 | |
| 147 | C | 1CO | 0.02526 | 0.24331 | 0.00649 | |
| 148 | O | 1OC | 0.01235 | 0.15545 | 0.00653 | |

EXAMPLE 12

Oxidation of Labyrinthopeptin (III)

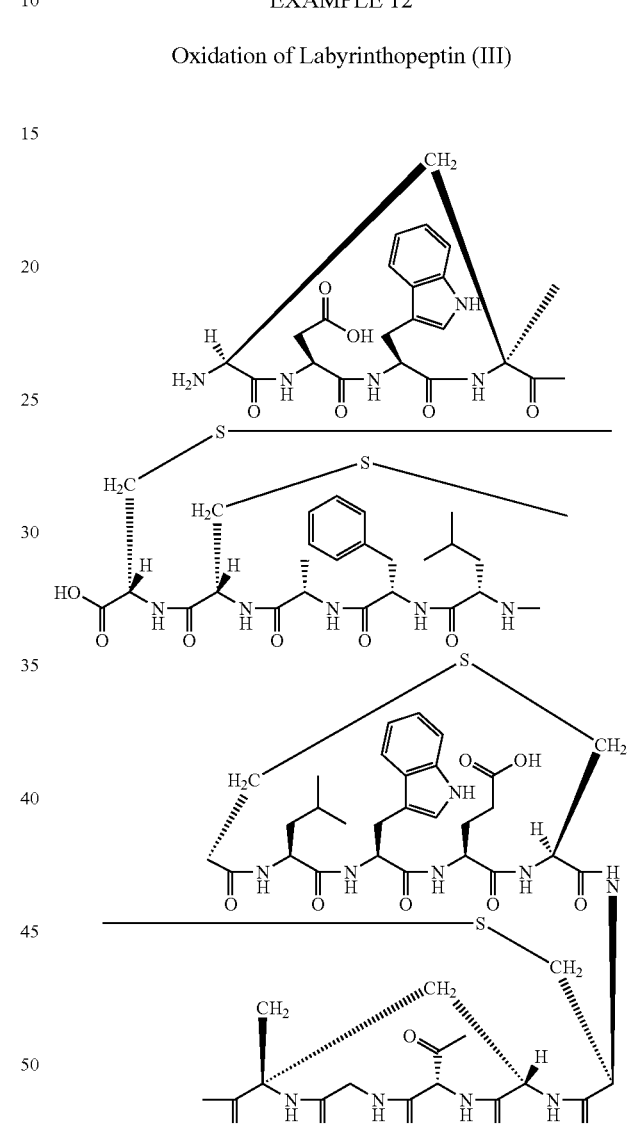

50 mg Labyrinthopeptin (III) (0.026 mmol) were dissolved in 1 ml DMSO and mixed with 11 mg 1-Hydroxy-1-oxide-1,2-Benziodoxol-3(1H)-one (IBX, 0.039 mmol) at room temperature. The mixture was stirred for 6 h at 40° C. and further 12 h at room temperature, and subsequently purified by reversed-phase HPLC on a Phenomenex Luna® Axia 5 μm C18 (2) column (dimension: 100 mm×30 mm) with a XTerra® Prep MS C18 10 μm pre-column (Waters, Dimension: 19×10 mm). A gradient of 5% to 95% acetonitrile in water over 30 min (containing 0.1% ammonium acetate, pH 7.0) was used as the eluent. Column flow (60 ml/min) was fractioned and by UV detection. Fraction 7 to 11 contained the desired compound. The said fractions yielded 25 mg (50%) after lyophilization. The product was characterized by mass spectroscopy (Bruker Daltonics Micro Tof).

UV: 222 sh, 278 nm
ESI-MS: MW=1920.66518 (mono MW)
Molecular formula: C,85; H,108; N,20; O,24; S,4
Molecular weight (MW)=1922.2

EXAMPLE 13

Peptide Synthesis on the C-terminal End of Labyrinthopeptins (III)

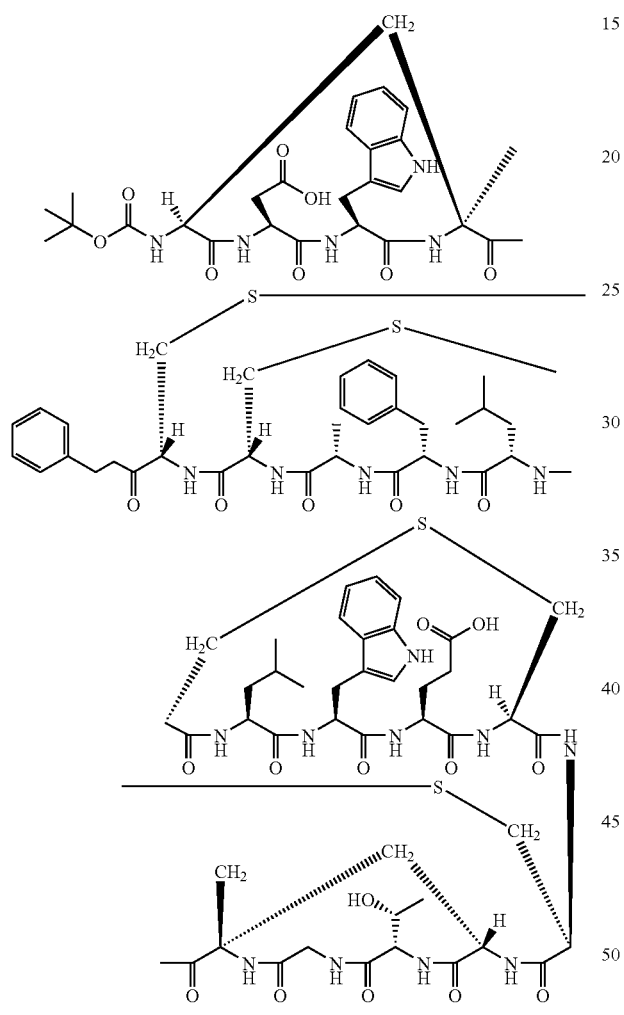

40 mg Labyrinthopeptin (III) (0.021 mmol) were dissolved in 2 ml absolute dimethylformamide and treated with 10 mg (0.045 mmol) di-tert-butyl-dicarbonate (Boc$_2$O) and 7 mg (0.054 mmol) diisopropylethylamine for 1 h at room temperature. Subsequently, 6.8 mg (0.063 mmol) benzylamine and 50 μl (0.072 mmol) a 50% solution of propyl phosphonic acid anhydride in DMF was added. The reaction mixture was purified via reversed-phase HPLC on a Waters XBridge Shield® 5 μm C18 Säule (dimension: 100 mm×30 mm) containing a XBridge Shield® C18 10 μm pre-column (Waters, dimension: 19×10 mm). A gradient of 5% to 95% acetonitrile in water over 30 min (containing 0.1% ammonium acetate, pH 7.0) was used as the eluent. Column flow (60 ml/min) was fractioned and by UV detection. Fractions 30 and 31 were combined and yielded 9.6 mg (22%) of the desired compound. The product was characterized by mass spectroscopy (Bruker Daltonics Micro Tof).

UV: 222 sh, 276 nm
ESI-MS: MW=2111.79018 (mono MW)
Molecular formula: C,97; H,125; N,21; O,25; S,4
Molecular weight (MW)=2113.5

EXAMPLE 14

Peptide synthesis on the N-terminal end of Labyrinthopeptins (III)

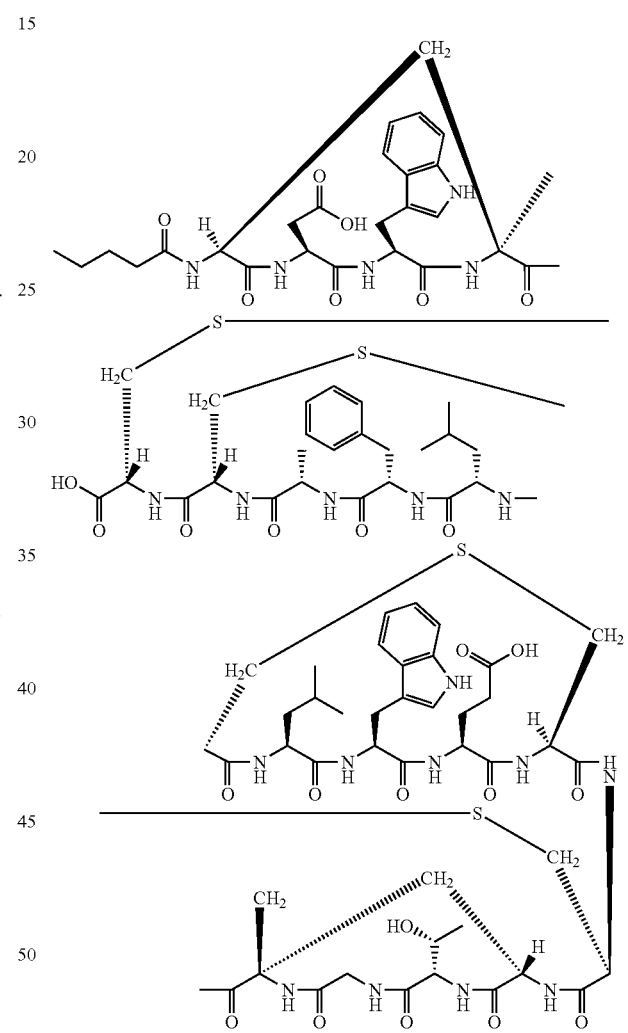

5 mg (0.028 mmol) 2-chloro-4,6-dimethoxy-1,3,5-triazin (CDMT) were dissolved in 2 ml abs. dimethylformamide and mixed with 8.6 mg (0.085 mmol) N-methylmorpholine (NMM). The mixture was stirred for 1 h at room temperature. 3.3 mg (0.028 mmol) n-capronic acid was added and the mixture stirred for further 30 min at room temperature. Subsequently, 40 mg (0.021 mmol) Labyrinthopeptin (III) was added and the resulting mixture was stirred for further 2 h at room temperature. The reaction mixture was purified via reversed-phase HPLC on a Waters XBridge Shield® 5 μm C18 Säule (dimension: 100 mm×30 mm) with a XBridge Shield® C18 10 μm pre-column (Waters, dimension: 19×10 mm). A gradient of 5% to 95% acetonitrile in water over 30 min (containing 0.1% formic acid, pH 2.0) was used as the eluent. Column flow (60 ml/min) was fractioned and by UV detection. Fractions 38 to 40 were combined and yielded 11.0 mg (26%) of the desired compound. The product was characterized by mass spectroscopy (Bruker Daltonics Micro Tof).

UV: 220 sh, 278 nm
ESI-MS: MW=2020.75738 (mono MW)
Molecular formula: C,91; H,120; N,20; O,25; S,4
Molecular weight (MW)=2022.3

EXAMPLE 15

Antibacterial Activity

After culturing the organisms in liquid beef extract broth, the suspensions of bacteria were adjusted to a defined density by dilution with fresh culture medium ($5 \cdot 10^5$ organisms/ml).

Labyrinthopeptin (III) was dissolved and diluted with water in a geometric dilution series (factor 2). 1.5 ml of the solution in the individual dilution steps were mixed with 13.5 ml liquid agar (Müller-Hinton agar) at approximately 45° C.

The maximum compound concentration in the petri dish was usually 100 mg/l. An agar plate with no compound served as a control.

After the culture medium had cooled and solidified, the agar plates were inoculated simultaneously with 20 different bacterial strains using a Multipoint Inoculator delivering $5 \cdot 10^4$ colony forming units (cfu) per inoculation spot and then incubated at 37° C. for 17 hours under aerobic conditions.

After incubation, the plates were examined macroscopically for the lowest compound concentration at which bacterial growth is no longer visible. A single colony or a haze growth at the inoculation spot was disregarded.

The antibacterial effect was assessed as the Minimum Inhibitory Concentration of the test compound (MIC: lowest compound concentration at which bacterial growth is no longer macroscopically visible):

| Test organism | MIC |
|---|---|
| *Staphylococcus aureus* SG 511 | 12.5 mg/l |
| *Staphylococcus aureus* 285 | 12.5 mg/l |
| *Staphylococcus aureus* 503 | 3.13 mg/l |
| *Streptococcus pyogenes* 308 A | 3.13 mg/l |
| *Streptococcus pyogenes* 77 A | 3.13 mg/l |
| *Streptococcus faecium* D | 6.25 mg/l |

EXAMPLE 16

Antiviral Activity

Viruses can only multiply in living cells. The viral studies were therefore carried out in cell cultures. The viruses were selected either because of their importance as infectious agents or typical biochemical or morphological structures.

A dilution series of Labyrinthopeptin (III) was prepared in 96-well microtiter plates. Hela or Vero cells, according to the infecting virus, are added to give a confluent monolayer within 24 h of incubation. After incubation for 3 hours, the respective virus is added to the cells in a concentration which is expected to completely destroy the cell monolayer within 2 days. The cultures are incubated at 37° C. in a gassed incubator (5% $CO_2$ in air). After 24 hours the maximal tolerated dose of test compound (MTD) in the cell culture is evaluated by microscopic examination. The results were compared with non-infected tissue control and a corresponding infection control:

| No. | Host organism | Test organism | Inhibition [mg/l] |
|---|---|---|---|
| 1 | Vero cells | Mycovirus (RNA/Influenza A/Aichi) | 44.44 |
| 2 | Hela cells | Herpes (DNA), Simples 1 | 133.33 |
| 3 | Vero cells | Herpes (DNA), Simplex 2 VR 734 | 44.44 |
| 4 | Hela cells | Adenovirus (DNA), 5" | 133.33 |

EXAMPLE 17

Neuropathic Pain Activity

Labyrinthopeptin (III) was studied in the spared nerve injury (SNI) mouse model of neuropathic pain in order to proof the activity on tactile allodynia. Under general anesthesia, the two major branches of the sciatic nerve in adult male C57B6 mice (22.7 g±0.26SEM) have been ligated and transected, with the sural nerve left intact. Tactile allodynia has been determined with the automatic von Frey test: using a dump needle stick, the plantar skin of hind paws was exposed to a pressure stimulus of increasing intensity up to 5 g. The force in grams at which the animal responded with hindpaw withdrawal was used as a read-out for tactile allodynia. The study was performed 7 days after nerve lesion over 6 hours with an additional measurement after 24 hours. Within two days after nerve transection, tactile allodynia developed completely and remained stable over at least two weeks. The compound was administered intravenous as a single application (3 mg/kg). As a vehicle for the intravenous application was the 1:1:18 (Ethanol:Solutol:phosphate buffered saline) vehicle chosen.

Paw withdrawal threshold (PWT) measurements have been used to calculate significant treatment effects, and for AUC calculations over a reference time period (6 hours) and subsequent % benefit calculations. For the statistical analysis the PWT values of the ipsilateral hind paws were used in two ways: first, with a 2-way ANOVA based on the PWT values for specific times (within a period of 24 hours) and second with a 1-way ANOVA on non-transformed delta AUC values |AUC1-6 hour|.

Two-way analysis of variance with repeated measures (Repeated factor: TIME, Analysis variable: PWT) followed by a Complementary Analysis (Effect of factor GROUP for each level of factor TIME (Winer analysis), Analysis variable: PWT) and a subsequent Dunnett's test for factor TREATMENT for each level of factor TIME (Two sided comparison vs. level VEHICLE) revealed highly significant differences from the vehicle group from 1 to 6 hours after intravenous application for each compound. The effect was gone 24 hours after application. 1-way ANOVA using delta |AUC1-6 hour| values revealed a p value of p<0.0001. Dunnett analysis and gave significant treatment effects for both compounds. The percent benefit of the treatment was evaluated using the |AUC1-6 hour| values of the ipsilateral vehicle group (0% benefit) and all |AUC1-6 hour| values of the contralateral sides of all three groups (100% benefit=maximal possible effect). Compared to these margins Labyrinthopeptin (III) achieved 97% benefit.

In conclusion, the compound significantly reduces tactile allodynia in the SNI mouse model of neuropathic pain.

EXAMPLE 18

Inflammatory Triggered Pain Activity

Labyrinthopeptin (III) was studied in the carrageenan (CAR) induced hindpaw inflammation model in mice in order to proof the activity on thermal hyperalgesia, a typical readout for inflammatory triggered pain.

Induction of hind paw inflammation: Under slight general Isofluran anesthesia, CAR 2% (Sigma, Deisenhofen, Germany) in 20 µl saline was injected into the plantar aspect of both hind paws in male C57B6 mice. Paw withdrawal latencies (PWL) were determined on exposure of the paws to a defined thermal stimulus using a commercially available apparatus (Plantar Test Ugo Basile Biological Research Apparatus, Comerio, Italy) fitted with a mini camera to ensure proper placement of the infrared heat below the hind paw of interest. Mice were kept in the test cages over the whole study period (6 hours).

Measurement of thermal hyperalgesia: The timer which measures the duration of reflecting infrared light by the hind paw is started by the investigator and stopped, if the animal is shaking the affected hind paw. A cut off was set at 16 seconds to prevent tissue damage. The study was performed before and over 6 hours after CAR injection. Paw withdrawal latencies in seconds were used as readout for further analysis.

As a vehicle for the intravenous application was the 1:1:18 (Ethanol:Solutol:phosphate buffered saline) vehicle chosen.

Paw withdrawal latencies (PWL) measurements have been used to calculate significant treatment effects, and for AUC calculations over a reference time period (6 hours) and subsequent % benefit calculations. For the statistical analysis the PWL values of both hindpaws were used in two ways: first, with a 2-way analysis of variance (ANOVA) based on the PWL values for specific times (within a period of 6 hours) and second with a 1-way ANOVA on non-transformed delta AUC values |AUC1-6 hour|.

Two-way Analysis of variance with repeated measures (Repeated factor: TIME, Analysis variable: PWL) followed by a Complementary Analysis (Effect of factor GROUP for each level of factor TIME (Winer analysis), Analysis variable: PWL) and a subsequent Dunnett's test for factor DOSAGE for each level of factor TIME (Two sided comparison vs. level 0=VEHICLE) revealed highly significant differences from the vehicle group from 1 to 2 hours after intravenous application for both dosages. The effect was gone 4 hours after application. 1-way ANOVA using delta |AUC1-6 hour| values revealed a p value of p<0.0001. Dunnett analysis and gave significant treatment effects for both dosages. The percent benefit of the treatment was evaluated using the |AUC1-6 hour| values of the vehicle group (0% benefit) and all |AUC1-6 hour| values before CAR was injected (theoretical baseline over 6 hours=maximum possible effect=100% effect). Compared to these margins the 1 mg/kg dosage group achieved 37 and the 10 mg/kg group 34% benefit.

In conclusion, the compound significantly reduced thermal hyperalgesia in the CAR mouse model of inflammatory triggered pain.

What is claimed is:

1. An isolated compound of the formula (I):

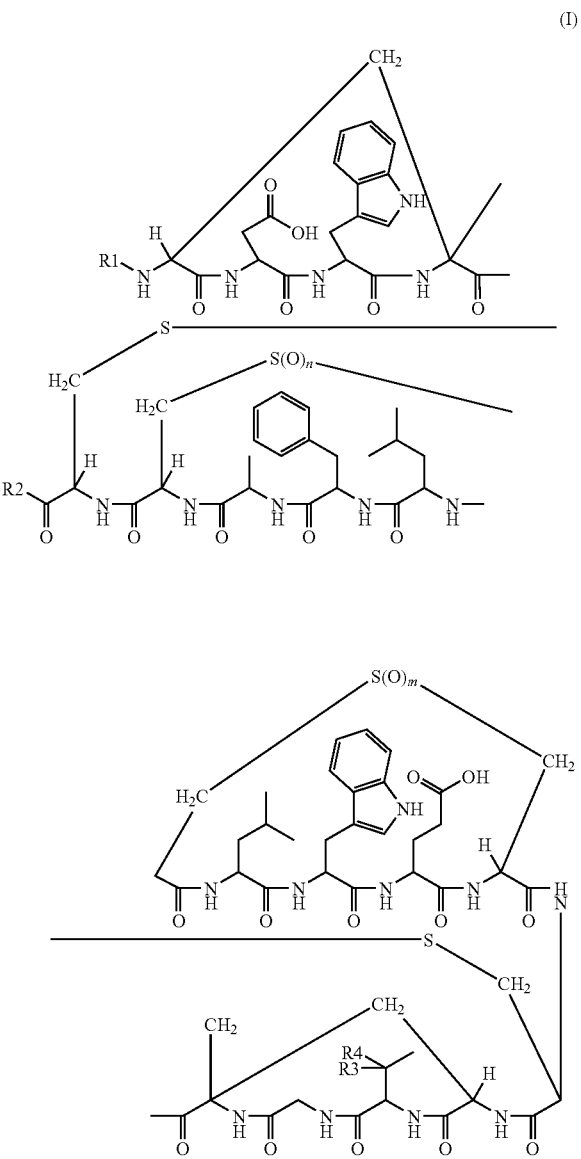

wherein
R1 is H, C(O)—(C$_1$-C$_6$)alkyl or C(O)—O—(C$_1$-C$_6$)alkyl;
R2 is OH, NH$_2$, NH—(C$_1$-C$_6$)alkyl, NH—(C$_1$-C$_4$)alkylene-phenyl or NH—(C$_1$-C$_4$)alkylene-pyridyl;
R3 and R4 are independently of each other H or OH, or R3 and R4 together are =O; and
m and n are independently of one another 0, 1 or 2; and
said compound being in any stereochemical form, or a mixture of any stereochemical forms in any ratio;
or a physiologically acceptable salt thereof.

2. The isolated compound according to claim 1 having the formula (II):

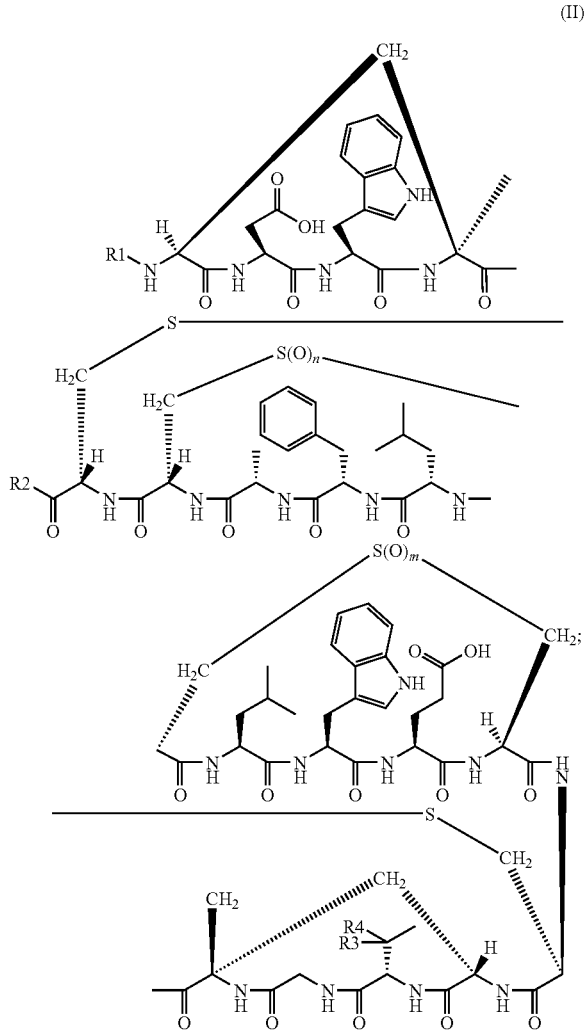

(II)

or a physiologically acceptable salt thereof.

3. The isolated compound according to claim 1 wherein R1 is H; or a physiologically acceptable salt thereof.

4. The isolated compound according to claim 2 wherein R1 is H; or a physiologically acceptable salt thereof.

5. The isolated compound according to claim 1 wherein R2 is OH; or a physiologically acceptable salt thereof.

6. The isolated compound according to claim 2 wherein R2 is OH; or a physiologically acceptable salt thereof.

7. The isolated compound according to claim 1 wherein R3 and R4 are H or OH and wherein if R3 is OH then R4 is H, or if R3 is H then R4 is OH, or R3 and R4 together are =O; or a physiologically acceptable salt thereof.

8. The isolated compound according to claim 2 wherein R3 and R4 are H or OH and wherein if R3 is OH then R4 is H, or if R3 is H then R4 is OH, or R3 and R4 together are =O; or a physiologically acceptable salt thereof.

9. The isolated compound according to claim 1 wherein R3 is OH and R4 is H, or R3 is H and R4 is OH; or a physiologically acceptable salt thereof.

10. The isolated compound according to claim 2 wherein R3 is OH and R4 is H, or R3 is H and R4 is OH; or a physiologically acceptable salt thereof.

11. The isolated compound according to claim 1 wherein m and n are both 0, or m and n are both 2, or m is 0 and n is 2, or m is 2 and n is 0; or a physiologically acceptable salt thereof.

12. The isolated compound according to claim 2 wherein m and n are both 0, or m and n are both 2, or m is 0 and n is 2, or m is 2 and n is 0; or a physiologically acceptable salt thereof.

13. The isolated compound according to claim 1 wherein m and n are both 0; or a physiologically acceptable salt thereof.

14. The isolated compound according to claim 2 wherein m and n are both 0; or a physiologically acceptable salt thereof.

15. The isolated compound according to claim 1 wherein R1 is H; R2 is OH; R3 and R4 are independently of each other H or OH wherein if R3 is OH then R4 is H, and if R3 is H then R4 is OH; and m and n are independently of one another 0, 1 or 2; or a physiologically acceptable salt thereof.

16. The isolated compound according to claim 2 wherein R1 is H; R2 is OH; R3 and R4 are independently of each other H or OH wherein if R3 is OH then R4 is H, and if R3 is H then R4 is OH; and m and n are independently of one another 0, 1 or 2; or a physiologically acceptable salt thereof.

17. The isolated compound according to claim 1 wherein R1 is H; R2 is OH; R3 and R4 are independently of each other H or OH wherein if R3 is OH then R4 is H, and if R3 is H then R4 is OH; and m and n are both 0, or m and n are both 2, or m is 0 and n is 2, or m is 2 and n is 0; or a physiologically acceptable salt thereof.

18. The isolated compound according to claim 2 wherein R1 is H; R2 is OH; R3 and R4 are independently of each other H or OH wherein if R3 is OH then R4 is H, and if R3 is H then R4 is OH; and m and n are both 0, or m and n are both 2, or m is 0 and n is 2, or m is 2 and n is 0; or a physiologically acceptable salt thereof.

19. The isolated compound according to claim 1 wherein R1 is H; R2 is OH; R3 and R4 are independently of each other H or OH and wherein if R3 is OH then R4 is H, and if R3 is H then R4 is OH; and m and n are both 0; or a physiologically acceptable salt thereof.

20. The isolated compound according to claim 2 wherein R1 is H; R2 is OH; R3 and R4 are independently of each other H or OH and wherein if R3 is OH then R4 is H, and if R3 is H then R4 is OH; and m and n are both 0; or a physiologically acceptable salt thereof.

21. The isolated compound according to claim 1 having the formula (III):

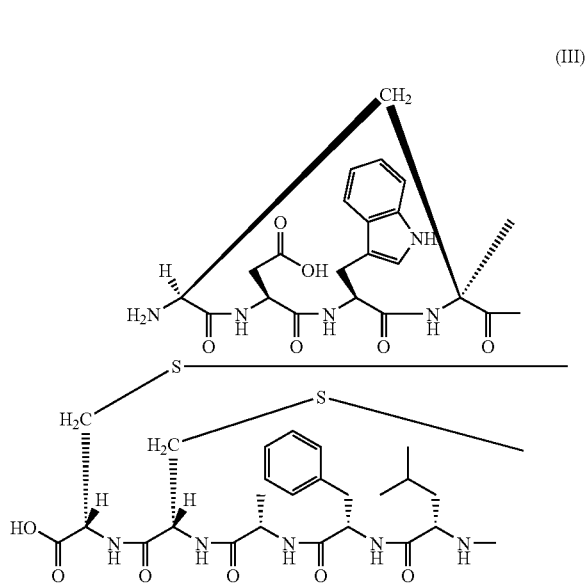

(III)

-continued

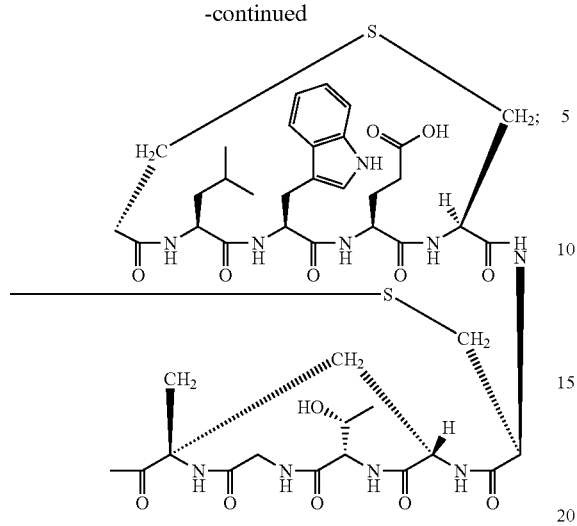

or a physiologically acceptable salt thereof.

22. The isolated compound according to claim 21, which is isolated from *Actinomadura namibiensis* (DSM 6313).

23. A method for treating a bacterial infection or pain comprising administering to a patient in need of said treatment a therapeutically effective amount of an isolated compound according to claim 1, or a physiologically acceptable salt thereof.

24. A pharmaceutical composition comprising at least one isolated compound according to claim 1, or a physiologically acceptable salt thereof, and at least one pharmaceutically acceptable ingredient.

25. A process for preparing an isolated compound of formula (I) according to claim 1 which comprises
   a) fermenting the strain *Actinomadura namibiensis* (DSM 6313) under suitable conditions in a culture medium until one or more of the compounds according to claim 1 of the formula (I) accrue(s) in the culture medium,
   b) isolating the compound according to claim 1 from the culture medium, and
   c) formulating the compound according to claim 1 of formula (I) into a physiologically acceptable salt where appropriate.

26. The process according to claim 25 wherein the isolated compound is of the formula (II):

(II)

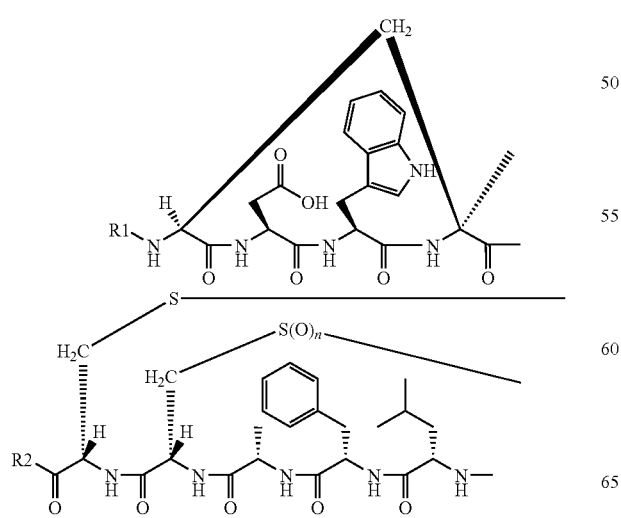

-continued

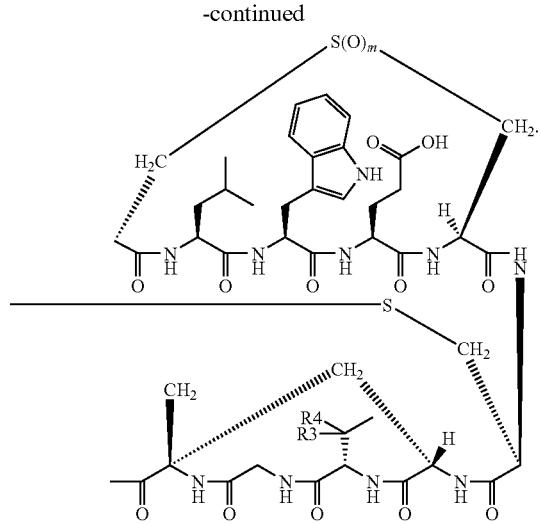

27. The process according to claim 25 wherein the isolated compound is of the formula (III):

(III)

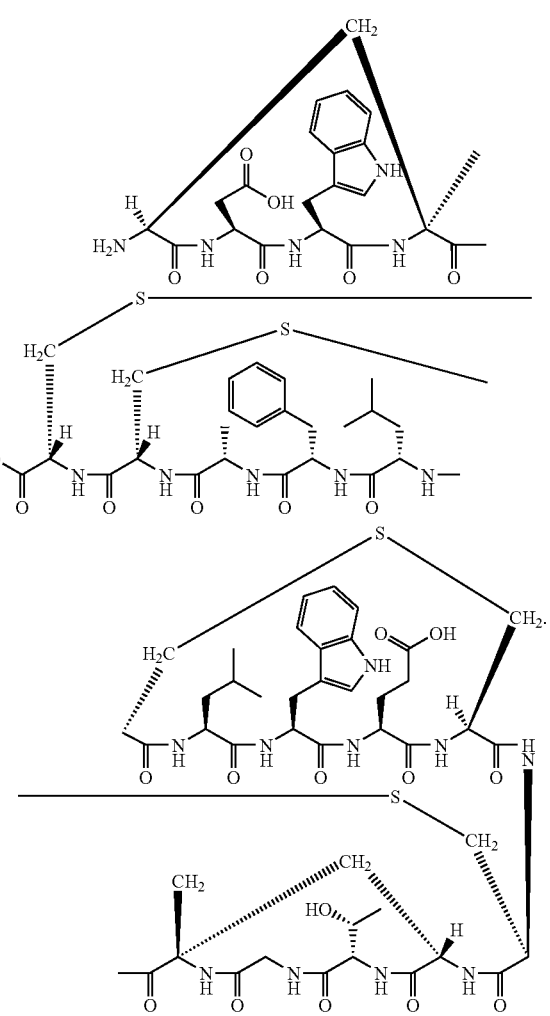

28. The process according to claim 25 wherein for the isolated compound according to claim 1, m and n are both 0, or m and n are both 2, or m is 0 and n is 2, or m is 2 and n is 0.

* * * * *